United States Patent [19]

Eenboom et al.

[11] Patent Number: 5,078,599
[45] Date of Patent: Jan. 7, 1992

[54] SYSTEM FOR INSPECTING A DENTAL MODEL

[75] Inventors: Algund Eenboom, Leer; Benedikt Pollock, Werne; Jürgen Lindigkeit, Herne, all of Fed. Rep. of Germany

[73] Assignee: Krupp Medizintechnik GmbH, Essen, Fed. Rep. of Germany

[21] Appl. No.: 505,943

[22] Filed: Apr. 6, 1990

[30] Foreign Application Priority Data

Apr. 8, 1989 [DE] Fed. Rep. of Germany ....... 3911568

[51] Int. Cl.$^5$ .............................................. A61C 1/00
[52] U.S. Cl. ......................................... 433/29; 433/215
[58] Field of Search .................... 433/29, 49, 55, 215, 433/229

[56] References Cited

U.S. PATENT DOCUMENTS

| 2,621,407 | 12/1952 | Schlesinger | 433/64 |
| 2,703,453 | 3/1955 | Landis | 433/29 |
| 2,759,264 | 8/1956 | Landis | 433/29 |
| 4,411,626 | 10/1983 | Becker et al. | 433/223 |
| 4,840,564 | 6/1989 | Segal | 433/72 |

FOREIGN PATENT DOCUMENTS

| 91876 | 10/1983 | European Pat. Off. | 433/29 |
| 1000961 | 1/1957 | Fed. Rep. of Germany . | |
| 2719696 | 11/1978 | Fed. Rep. of Germany . | |
| 3331262 | 3/1989 | Fed. Rep. of Germany . | |
| 3528621 | 3/1989 | Fed. Rep. of Germany . | |
| 1364331 | 1/1988 | U.S.S.R. | 433/49 |
| 2030868 | 4/1980 | United Kingdom | 433/29 |
| 2197955 | 6/1988 | United Kingdom | 433/55 |

Primary Examiner—Gene Mancene
Assistant Examiner—Michael Lynch
Attorney, Agent, or Firm—Herbert Dubno; Andrew M. Wilford

[57] ABSTRACT

A method of inspecting a positive dental model having an impression plane comprises the step of first projecting a small beam of light of predetermined cross section on individual teeth of the model generally perpendicular to the impression plane, that is the plane perpendicular to which the impression fork was fitted to and removed from the patient's jaw. Thus the beam forms on each tooth a spot having a shape dependent on the contours of the respective tooth and the inclination of the respective tooth surface to the beam. The spot is moved from tooth to tooth on the model and the shapes of the spots of the beam on adjacent teeth are compared. If the shape changes, the teeth are not parallel and if there is a shadow or interruption of the teeth there is an undercut, and both conditions have to be corrected by regrinding the patient's tooth stumps. Similarly as the spot is moved, it can be used to measure the height and width of the teeth, the space between them, and even the overall arch length.

19 Claims, 1 Drawing Sheet

SYSTEM FOR INSPECTING A DENTAL MODEL

FIELD OF THE INVENTION

The present invention relates to a system for inspecting or testing a dental impression or model. More particularly this invention concerns measuring such an impression or model.

BACKGROUND OF THE INVENTION

In order to be able to properly mount a dental prostheses such as a bridge or a crown the teeth must be accurately filed down to frustoconical stumps having no undercuts. In addition it is necessary that each tooth stump be centered on an axis parallel to the axes of the adjacent stumps so that the part being installed can be slipped on parallel to these axes.

A positive dental model of the jaw portion with the ground-down tooth stumps is typically examined by the technician to check for undercuts or nonparallel stumps. Clearly the quality of such a visual examination depends on the experience of the person doing it.

It is also known to test for parallelism by running a sensing finger of a special testing apparatus around each stump. Not only is this system fairly complex and does it require expensive equipment, but it is relatively crude, not picking up small variations. In addition to the high cost, the stumps in the patient's mouth must frequently be reworked before the bridge or crown can be installed. In addition it is often necessary to diagnose whether when teeth are missing there is room available once the teeth have been reworked. To date the dental models are measured by means of calipers and the necessary sizes are calculated separately.

Digital calipers are known which are connected to a personal computer to take the necessary measurements. The accuracy of this procedure is also inadequate. Measuring teeth arches is not possible, so this measurement is traditionally done by lying a wire on the teeth and subsequently measuring the rectified length of the wire.

OBJECTS OF THE INVENTION

It is therefore an object of the present invention to provide an improved method of and apparatus for checking a dental impression.

Another object is the provision of such an improved method of and apparatus for checking a dental impression which overcomes the above-given disadvantages, that is which accurately finds undercuts and that is easy to use.

SUMMARY OF THE INVENTION

A method of inspecting a positive dental model having an impression plane according to this invention comprises the step of first projecting a small beam of light of predetermined cross section on individual teeth of the model generally perpendicular to the impression plane, that is the plane perpendicular to which the impression fork was fitted to and removed from the patient's jaw. Thus the beam forms on each tooth a spot having a shape dependent on the contours of the respective tooth and the inclination of the respective tooth surface to the beam. The spot is moved from tooth to tooth on the model and according to the invention the shapes of the spots of the beam on adjacent teeth are compared.

If the shape changes, the teeth are not parallel and if there is a shadow or interruption of the teeth there is an undercut, and both conditions have to be corrected by regrinding the patient's tooth stumps. Similarly the spot can be moved in steps along the bridge area in question so that it can be used to measure the height and width of the teeth, the space between them, and even the overall arch length.

The beam according to this invention is columnar and circular and at most 0.6mm in diameter. It is formed by a helium-neon laser beam. In addition the beam can be projected through a measurement grid for accurately determining dimensions on the model. In addition differently sized spots, formed by passage through differently sized holes in the grid, can be used to accurately determine what if any reworking of the patient's mouth is necessary.

The apparatus according to the invention therefore has a support for holding the model generally stationary, a light source for projecting a small beam of light of predetermined cross section on individual teeth of the model generally perpendicular to the impression plane, and some other support for movement of the light source parallel to the impression plane.

In accordance with further features of the invention a common frame carries the support for the model and the means for movement of the source. This frame includes a column having a lower portion provided with the support and an upper portion having a vertically adjustable arm constituting the means for movement. The frame includes a base into which the column is set and on which the support is mounted.

The support itself in accordance with this invention includes a ball joint so that the orientation of the plane of the model can be adjusted. A pivotal loupe is carried on the arm along with a shutter-free lamp. The arm is articulated about at least one axis parallel to the beam.

The model support is movable in x- and y-directions orthogonal to the beam and to each other and is even tippable through 90° for displacement in a z-direction orthogonal to the x- and y-directions. The support is provided with sensors for movement in the directions and a computer or printer is connected to the sensors for receiving outputs therefrom and plotting the teeth.

DESCRIPTION OF THE DRAWING

The above and other objects, features, and advantages will become more readily apparent from the following, reference being made to the accompanying drawing in which.

SPECIFIC DESCRIPTION

Figure 1:
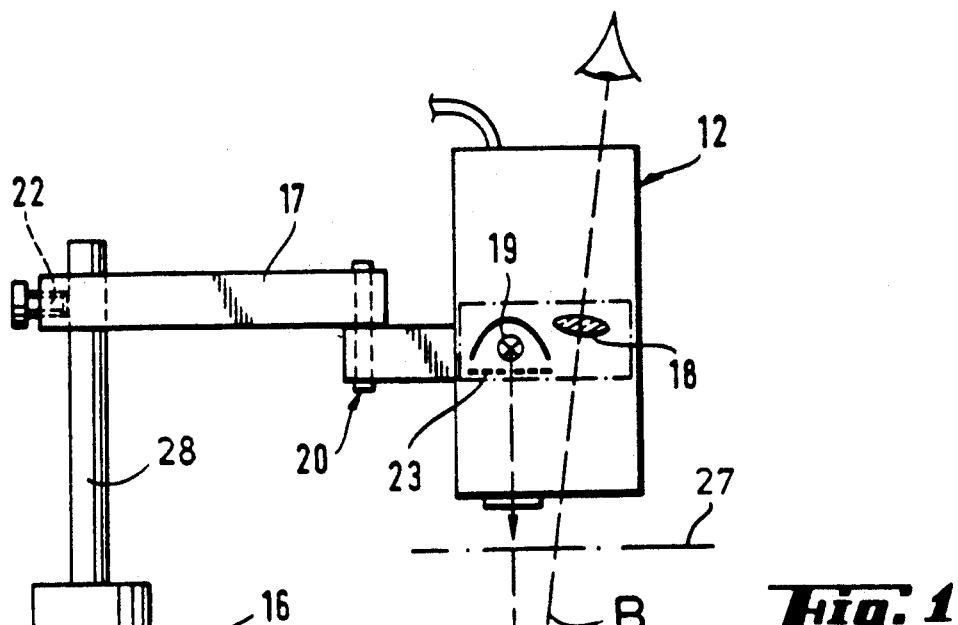
FIG. 1 is a largely schematic side view of the apparatus according to this invention.

As seen in FIG. 1 an apparatus according to this invention basically comprises a support table 10 for a positive dental model 11 taken perpendicular to an impression plane P and a laser-light source 12 thereabove. A base 13 carries a plate 14 on which a ball-type swivel joint 15 holds the support 10 so that the angle of the bridge arch being examined can be set horizontal and perpendicular to a vertical beam B emitted by the source 12. This base 13 has a mast 16 in which is set a post 28 to which a two-part outrigger arm 17 carrying the laser 12 is secured. The vertical position of the arm 17 on the post 28 can be changed, and a lock screw 22 is provided for securing it in place once the desired position is obtained.

The light source 12 can be moved horizontally by swiveling of the arm 17 at its elbow joint 20 and/or by swiveling of the post 28 about its vertical axis in the mast 16. This source 12 also carries a magnifying glass or lens 18 and a antidazzle lamp 19. Furthermore a millimeter grid can be positioned at 27 in the beam B emitted by the laser 12 for comparison purposes. This laser 12 is of the helium-neon type and the beam B is circular with a diameter of at most 0.6mm.

Figure 2:
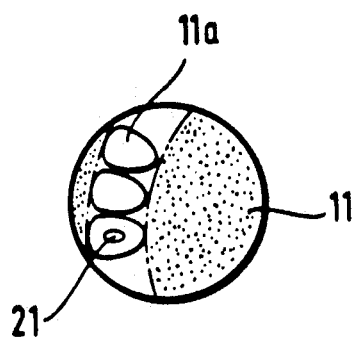
FIG. 2 is a large-scale view of the detail indicated at D2 in FIG. 1.

Thus as seen in FIG. 2 when the beam B forms a noncircular spot 21 on a tooth 11a the general dimensions, which can be ascertained by means of the grid 27, of the spot 21 and the direction of its major axis readily determine the shape, size, and inclination of the tooth stump. As the laser source 12 is moved horizontally to scan the adjacent teeth any change in this shape or the orientation of its major axis indicates nonparallelism of the teeth. Furthermore any undercut will show up clearly as a shadow.

It is also possible to provide the table 10 with adjustment wheels such as shown at 23 for moving it along x and y axes, and to provide sensors 24 and 25 which read out the x- and y-axis positions to a computer 26. The dimensions at each location are fed into the computer 26, and the table 10 can be tipped 90° to also read out along the z axis, giving a dimension for the lengths of the tooth stumps also.

We claim:

1. A method of inspecting a positive dental model having an impression plane, the method comprising the steps of:
    projecting a small beam of light of predetermined cross section on individual teeth of the model generally perpendicular to the impression plane, whereby the beam forms on each tooth a spot having a shape dependent on the contours of the respective tooth and the inclination of the respective tooth surface to the beam;
    moving the spot from tooth to tooth on the model; and
    comparing the shapes of the spots of the beam on adjacent teeth.

2. The method defined in claim 1 wherein the beam is columnar and circular and at most 0.6mm in diameter.

3. The method defined in claim 1 wherein the beam is a helium-neon laser beam.

4. The method defined in claim 1, further comprising the step of
    projecting the beam through a measurement grid.

5. The method defined in claim 1, further comprising the step of
    moving the beam along a region of the model and thereby measuring the length of the path followed by the beam, whereby the length, width, or height of the region can be determined.

6. An apparatus for inspecting a positive dental model having an impression plane, the apparatus comprising:
    a support for holding the model generally stationary;
    means including a laser light source for projecting a small columnar beam of laser light of predetermined cross section on individual teeth of the model generally perpendicular to the impression plane, whereby the beam forms on each tooth a spot having a shape dependent on the contours of the respective tooth and the inclination of the respective tooth surface to the beam; and
    means for movement of the light source parallel to the plane, whereby the spot can be projected on successive teeth of the model.

7. The apparatus defined in claim 6 wherein the beam is circular and has a diameter of at most 0.6mm.

8. The apparatus defined in claim 6 wherein the source is a helium-neon laser.

9. The apparatus defined in claim 8 wherein the support includes a ball joint, whereby the orientation of the plane of the model can be adjusted.

10. The apparatus defined in claim 6, further comprising
    a common frame carrying the support for the model and the means for movement of the source.

11. The apparatus defined in claim 10 wherein the frame includes a column having a lower portion provided with the support and an upper portion having a vertically adjustable arm constituting the means for movement.

12. The apparatus defined in claim 11 wherein the frame includes a base into which the column is set and on which the support is mounted.

13. The apparatus defined in claim 9, further comprising a pivotal loupe carried on the arm.

14. The apparatus defined in claim 11 wherein the loupe is provided with a shutter-free lamp.

15. The apparatus defined in claim 9 wherein the arm is articulated about at least one axis parallel to the beam.

16. The apparatus defined in claim 6, further comprising
    a measurement grid supported in the beam between the source and the model.

17. The apparatus defined in claim 16 wherein the model support is tippable through 100° for displacement in a z-direction orthogonal to the x- and y-directions and is provided with sensors for movement in the directions.

18. The apparatus defined in claim 17, further comprising output means connected to the sensors for receiving outputs therefrom and plotting the teeth.

19. The apparatus defined in claim 6 wherein the support includes means for moving it in x- and y-directions orthogonal to the beam and to each other.

* * * * *